US009627912B2

(12) United States Patent
Wood et al.

(10) Patent No.: US 9,627,912 B2
(45) Date of Patent: Apr. 18, 2017

(54) MOBILE CART WITH CAPACITIVE POWER SUPPLY

(71) Applicant: Welch Allyn, Inc., Skaneateles Falls, NY (US)

(72) Inventors: Robert J. Wood, Syracuse, NY (US); Ian K. Edwards, Skaneateles Falls, NY (US); Raymond A. Lia, Auburn, NY (US); Jon R. Salvati, Skaneateles Falls, NY (US); Robert L. Vivenzio, Auburn, NY (US); Miguel C. Mudge, Syracuse, NY (US); Michael Curry, Syracuse, NY (US); Shawn St. Pierre, Syracuse, NY (US)

(73) Assignee: Welch Allyn, Inc., Skaneateles, NY (US)

( * ) Notice: Subject to any disclaimer, the term of this patent is extended or adjusted under 35 U.S.C. 154(b) by 556 days.

(21) Appl. No.: 13/718,869

(22) Filed: Dec. 18, 2012

(65) Prior Publication Data

US 2014/0167506 A1     Jun. 19, 2014

(51) Int. Cl.
*H02J 7/02* (2016.01)
*H02J 7/00* (2006.01)
*H02J 7/34* (2006.01)

(52) U.S. Cl.
CPC .............. *H02J 7/02* (2013.01); *H02J 7/0014* (2013.01); *H02J 7/0026* (2013.01); *A61B 2560/0209* (2013.01); *A61B 2560/0214* (2013.01); *H02J 7/345* (2013.01); *H02J 2007/004* (2013.01); *H02J 2007/0039* (2013.01); *Y10T 307/359* (2015.04)

(58) Field of Classification Search
CPC .................................... G05F 1/00; G05F 1/66
USPC ............................................................. 307/25
See application file for complete search history.

(56) References Cited

U.S. PATENT DOCUMENTS

| | | | |
|---|---|---|---|
| 5,301,659 A * | 4/1994 | Brisson ............. | A61B 17/2255 600/439 |
| 5,808,376 A * | 9/1998 | Gordon .................. | G01T 1/175 307/64 |
| 5,850,113 A | 12/1998 | Weimer et al. | |
| 6,016,049 A | 1/2000 | Baughman et al. | |
| 6,373,152 B1 | 4/2002 | Wang et al. | |
| 6,424,156 B1 | 7/2002 | Okamura | |
| 6,546,286 B2 | 4/2003 | Olson | |
| 7,649,344 B2 | 1/2010 | Bang et al. | |
| 7,786,620 B2 | 8/2010 | Vuk et al. | |
| 8,106,533 B1 | 1/2012 | Johnson | |
| 2004/0004462 A1 * | 1/2004 | Bean et al. .................. | 320/128 |

(Continued)

OTHER PUBLICATIONS

PCT International Searching Authority; International Search Report and Written Opinion for International application No. PCT/US2013/074355; mailed on Apr. 23, 2014, 12 pages.

(Continued)

*Primary Examiner* — Thienvu Tran
*Assistant Examiner* — David M Stables
(74) *Attorney, Agent, or Firm* — Merchant & Gould P.C.

(57) ABSTRACT

A mobile system includes a mobile cart and an electronic device supported by the mobile cart. The mobile cart includes integral power storage structures that store electrical energy. The mobile cart also includes power supply electronics configured to supply the electrical energy to the electronic device to power the electronic device.

20 Claims, 7 Drawing Sheets

(56) References Cited

U.S. PATENT DOCUMENTS

| | | | |
|---|---|---|---|
| 2005/0281377 A1* | 12/2005 | Heinze | H05G 1/10 |
| | | | 378/101 |
| 2007/0139018 A1 | 6/2007 | Mentelos | |
| 2010/0264738 A1* | 10/2010 | Murtha | G06F 1/263 |
| | | | 307/66 |
| 2011/0279958 A1* | 11/2011 | Clark | A61B 5/0002 |
| | | | 361/679.02 |
| 2012/0068542 A1 | 3/2012 | Alappat | |
| 2012/0080944 A1 | 4/2012 | Recker et al. | |
| 2012/0175209 A1 | 7/2012 | Mazumdar et al. | |

OTHER PUBLICATIONS

Kim, Y., "Ultracapacitor Technology Powers Electronic Circuits," *Power Electronics Technology*, pp. 34-39 (Oct. 2003).

Maher, B., "Ultracapacitors: The Battery-less, High Reliability Back-up Solution," *Twenty-Seventh International Telecommunications Conference*, pp. 321-326 (Sep. 2005).

\* cited by examiner

MOBILE CART WITH CAPACITIVE POWER SUPPLY

BACKGROUND

Medical instruments, such as a patient monitor, are commonly used by medical caregivers. In such use, it is often helpful for the medical instruments to be arranged on a mobile cart to permit the instrument to be easily moved around within a facility. For example, a care provider can be assigned to a patient monitor, which the care provider can keep with him or her during a shift.

A drawback with using medical instruments in a mobile manner, however, is that electrical energy is not readily available. Medical instruments may have batteries, but the batteries may not last for an entire shift. Even if they do, a substantial amount of time is required to recharge the batteries. This may require that multiple medical instruments be obtained so that one of the instruments can be used while the other instrument is recharged, for example.

SUMMARY

In general terms, this disclosure is directed to a mobile cart. In one possible configuration and by non-limiting example, the mobile cart includes an integral capacitive power supply that can be used to power an electronic device supported by the mobile cart.

One aspect is a mobile cart comprising a wheeled base section; a support structure extending vertically upward from the base, the support structure having an interior space; a plurality of capacitor power storage devices arranged in the interior space of the support structure; and power supply electronics including: input circuitry configured to receive electrical energy from an external power source and to recharge the capacitor power storage devices; and output circuitry configured to supply electrical energy from the capacitor power storage devices to power an electronic device supported by the mobile cart.

Another aspect is a mobile system comprising: a medical instrument; and a mobile cart supporting the medical instrument, the mobile cart comprising: a wheeled base section; a support structure extending vertically upward from the base, the support structure having an interior space; a plurality of capacitor power storage devices arranged in the interior space of the support structure; and power supply electronics including: input circuitry configured to receive electrical energy from an external power source and to recharge the capacitor power storage devices; and output circuitry electrically coupled to the medical instrument to supply electrical energy from the capacitor power storage devices to the medical instrument.

A further aspect is a method of powering an electronic device with a mobile cart, the method comprising: receiving energy at the mobile cart from an external source; storing the energy in capacitors, the capacitors being positioned within an interior space of the mobile cart; converting the energy from the capacitors into a form suitable for delivery to the electronic device; and supplying the energy to the electronic device from the mobile cart.

DETAILED DESCRIPTION

Figure 1:
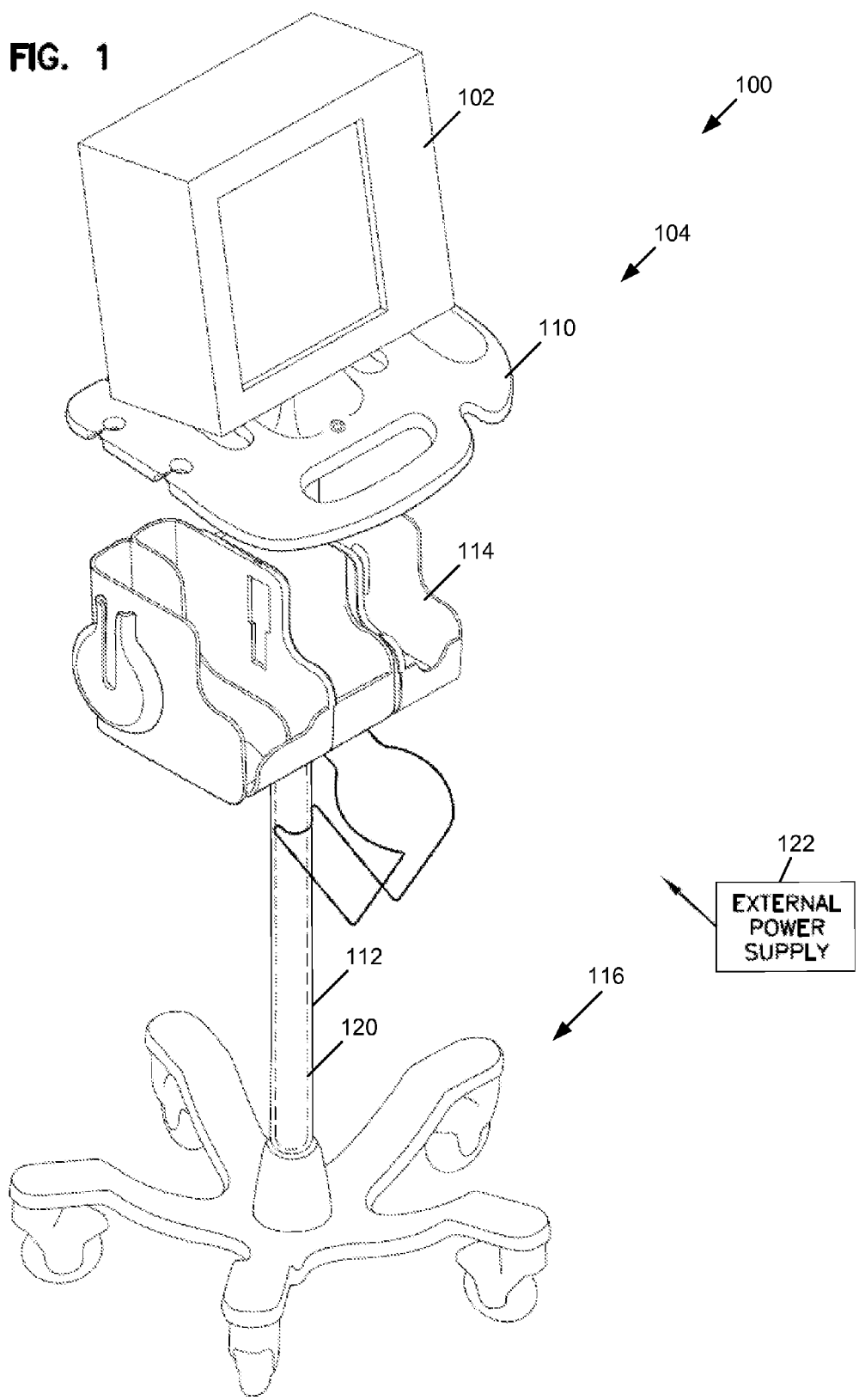
FIG. 1 is a perspective front view of an example mobile system according to the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The present disclosure relates to a mobile cart having an integral power supply. The mobile cart is configured to support one or more electronic devices thereon, and is also used to store and supply electricity to the electronic devices. In some embodiments, the power supply includes a plurality of capacitors which can be rapidly recharged, such as to reduce down time.

FIG. 1 is a perspective front view of an example mobile system 100. In this example, the mobile system includes an electronic device 102 and a mobile cart 104. The example mobile cart 104 includes a stand 110, a support structure 112, a storage region 114, and a wheeled base 116. In addition, the mobile cart 104 includes an integral power supply 120. Also illustrated in FIG. 1 is an external power source 122.

In some embodiments, the mobile cart 104 is arranged and configured to support and supply electricity to an electronic device 102. The electronic device 102 is a device including electronics that are powered by electricity.

An example of an electronic device 102 is a medical instrument. A wide variety of medical instruments can be used in various embodiments. One example of a medical instrument is a vital signs monitor, which includes one or more sensors for detecting signals and monitoring one or more vital signs of a patient, such as pulse rate, blood pressure, temperature, respiratory rate, and oxygen saturation. A more specific example of a vital signs monitor is the CONNEX® Vital Signs Monitor 6000 Series, available from Welch Allyn, Inc of Skaneateles Falls, N.Y.

The mobile cart 104 provides a sturdy support structure for supporting one or more of the electronic devices 102 thereon. In this example, and as noted above, the mobile cart includes the stand 110, the support structure 112, the storage region 114, and the wheeled base 116.

The stand 110 is arranged and configured to physically connect to the electronic device 102. In some embodiments, the stand 110 includes a substantially horizontal platform including an upper surface that provides a platform on which the electronic device 102 or other devices or objects can be placed thereon. In some embodiments, the stand 110 includes one or more fastening features, such as fingers, recesses, clips, clasps, mounting holes, or the like that are used to physically connect the electronic device 102 with the stand 110 to securely support the electronic device 102 when in use or transport.

The support structure 112 is a structure that connects to and supports the stand in an elevated position above the wheeled base 116. In some embodiments, the support structure 112 includes a hollow tube that is arranged substantially vertical. A lower portion of the support structure 112 is coupled to the wheeled base 116, and an upper portion of the support structure 112 is coupled to the stand 110.

The storage region 114 is included in some embodiments and is coupled to a central region of the support structure 112 between the lower portion and the upper portion. The storage region 114 provides storage compartments that can be used to store additional electronic devices or other objects, such as patient records, user manuals, procedure manuals, and the like.

The wheeled base 116 forms the base support structure of the mobile cart 104. In some embodiments, the wheeled base 116 includes a plurality of legs extending radially outward from a center, where it is connected to the support structure 112. Wheels, such as lockable swivel casters, are connected to the distal ends of the legs. The wheeled base 116 permits the mobile system 100 to be easily transported around a facility, such as a medical facility, so that the mobile system 100 can be used in various locations within the facility as needed.

The mobile cart 104 also includes a power supply 120 that is at least partially contained within the support structure 112. In some embodiments, an additional portion of the power supply 120 is contained within the storage region 114.

Also shown in FIG. 1 is an external power source 122. The external power source 122 is not a part of the mobile system 100. However, in some embodiments the mobile cart 104 is electrically or inductively connected to the external power source 122 to recharge the power supply 120. An example of the external power source 122 is mains power. For example, the mobile cart 104 can be connected to the external power source 122 through a power cable and plug connected to a wall receptacle. Charging stations can also be provided in some embodiments to provide quick and convenient recharging of the mobile cart 104. Other external power sources 122 can also or alternatively be used, such as a solar panel, a battery, or any other external power source suitable for supplying electrical energy to the mobile system 100.

Figure 2:
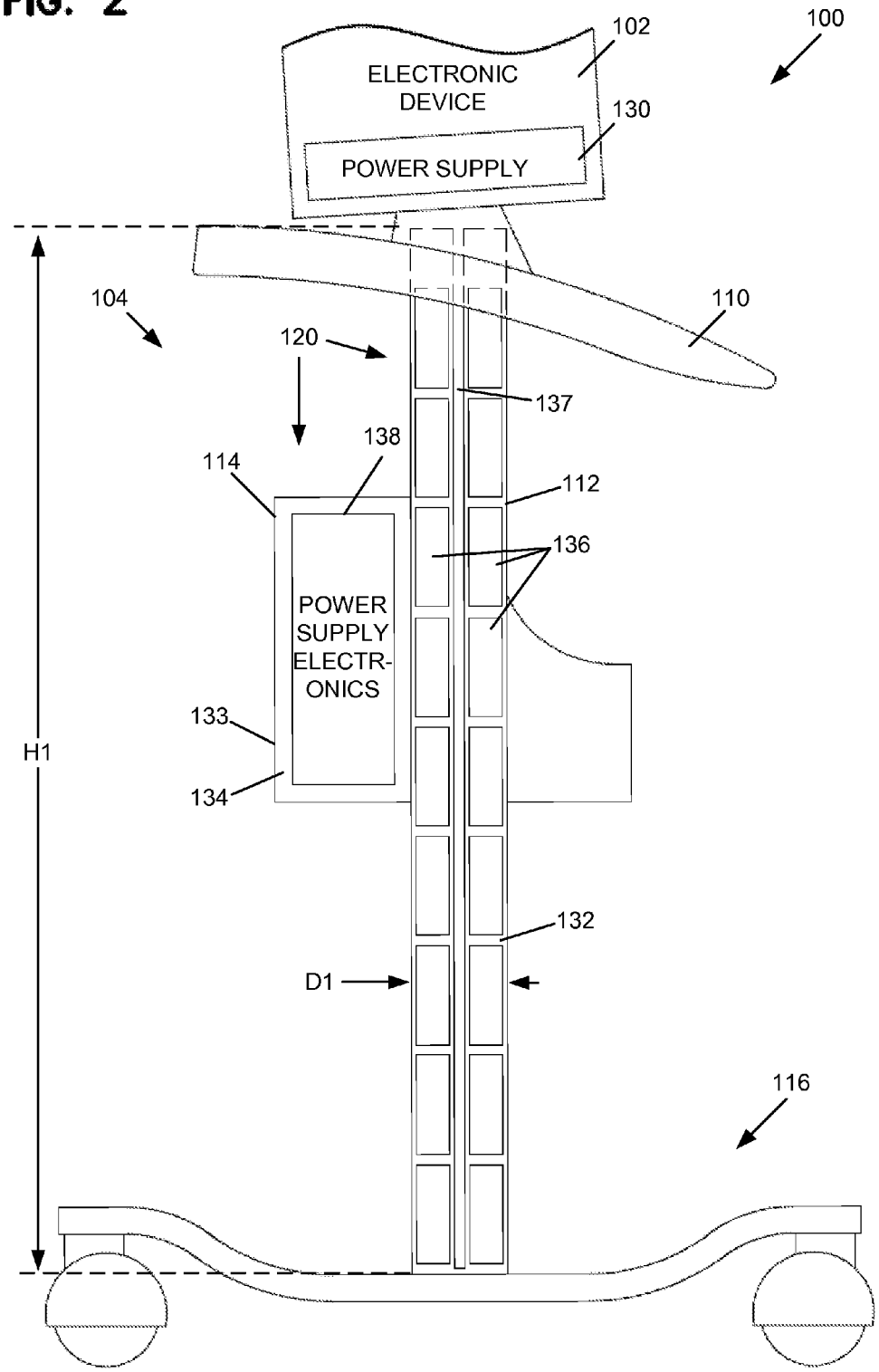
FIG. 2 is a schematic cross-sectional side view of the example mobile system shown in FIG. 1.
Figure 3:
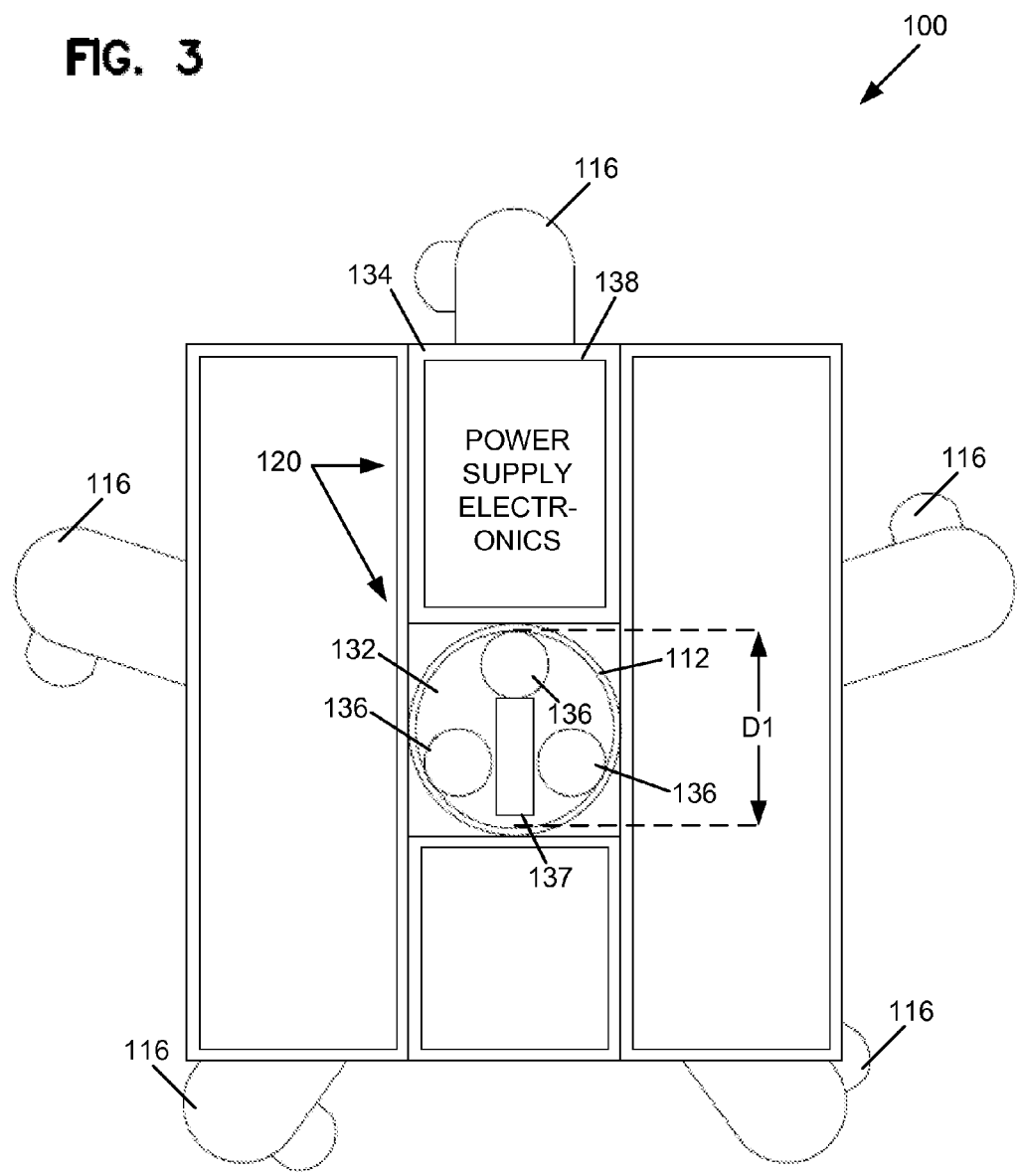
FIG. 3 is a schematic cross-sectional top view of the example mobile system shown in FIG. 1.

FIGS. 2-3 illustrate additional details of the example mobile system 100. FIG. 2 is a schematic cross-sectional side view of the example mobile system 100. FIG. 3 is a schematic cross-sectional top view of the example mobile system 100.

As discussed above, the example mobile system 100 includes the electronic device 102 and the mobile cart 104. The mobile cart 104 includes the stand 110, the support structure 112, the storage region 114, and the wheeled base 116.

Also illustrated in FIGS. 2-3 is the power supply 130 of the electronic device 102, the interior space 132 of the support structure 112, the interior space 134 of a compartment 133 of the storage region 114, and the power supply 120. In this example, the power supply 120 of the mobile cart 104 further includes power storage devices 136 and power supply electronics 138.

In some embodiments, the electronic device 102 includes a power supply 130. The power supply 130 includes a power storage device, such as one or more batteries and/or capacitors. The power supply 130 temporarily stores energy for powering the electronic device 102. As discussed herein, in some embodiments the mobile cart 104 operates to recharge the power supply 130. In yet another possible embodiment, however, the mobile cart 104 operates to power the electronic device 102 directly, such that the electronic device 102 does not include the power supply 130 in some embodiments.

In some embodiments, the support structure 112 is a hollow structure having defining an interior space 132. The size and shape of the interior space can be adjusted in various embodiments depending on the size of the support structure 112 used. The interior space 132 of the support structure 112 can have any desired cross-sectional shape, such as squared, rectangular, circular, oval, triangular, and the like. In some embodiments, the support structure 112 has an interior space having a cross-sectional distance D1 and a height H1. In some embodiments, the cross-sectional distance D1 is in a range from about 2" to about 5". Some embodiments have a cross-sectional distance D1 of about 3". In some embodiments, the height H1 is in a range from about 2 feet to about 6 feet. Some embodiments have a height H1 of about 4 feet. Other embodiments have other dimensions. As a result, the volume of the interior space can be substantial. For example, the volume of a 4 foot tall cylindrical support structure having a 3 inch diameter is more than 300 cubic inches.

In this example, the storage region 114 also includes a compartment 133 defining an interior space 134. In this example, the compartment 133 is located behind the support structure 112 and between side storage compartments of the storage region. However, the compartment 133 can have other positions or configurations in other embodiments.

In some embodiments, the power supply 120 of the mobile cart 104 includes power storage devices 136 and power supply electronics 138 which are enclosed within the interior space of the mobile cart 104, such as within one or more of the interior space 132 of the support structure 112 and the interior space 134 of the storage region 114.

In order to supply power to the electronic device 102 when the mobile cart 104 is disconnected from an external power source 122 (shown in FIG. 1), the power supply 120 includes power storage devices 136. The power storage devices 136 are any devices capable of storing electrical energy. In an example embodiment, the power storage devices 136 are capacitors, although batteries or other power storage devices can be used in other embodiments. In some embodiments, the power storage devices 136 are large capacity capacitors, such as the general types of capacitors referred to as super capacitors or ultra capacitors. The capacitors can be of any one of a variety of packaging types, such as can style capacitors (having a generally cylindrical shape) or prismatic type (having a generally rectangular shape). In some embodiments, such large capacity capacitors have capacitances of greater than about 100 Farads. Some embodiments utilize capacitors having capacitances in a range from about 100 Farads to about 1000 Farads. Other embodiments utilize capacitors having different capacitances, including capacitances less than 100 Farads and capacitances greater than 1000 Farads.

In some embodiments, the power storage devices 136 are housed within the interior space of the mobile cart, such as within the interior space 132 of the support structure 112. Due to the potentially substantial volume of the interior space 132, many power storage devices 136 can be arranged within the interior space 132, in some embodiments. For example, in some embodiments the quantity of power storage devices 136 is in a range from about 10 to about 50 power storage devices 136. However, a single large power storage device 136 can be used in another possible embodiment, or in a range from 1 to 10 in another embodiment, or greater than 50 in yet another embodiment.

Collectively, the power storage devices 136 can provide a significant capacitance. For example, the combined capacity of the power storage devices is in a range from about 1,000 Farads to about 50,000 Farads, in some embodiments.

One advantage of using capacitors is that capacitors can be recharged very rapidly. In fact, the rate at which the capacitors are recharged is typically primarily limited by the electrical conductors used to supply the energy to the capacitors, or by the amount of energy that can be supplied by the external power source 122. Accordingly, in some embodiments recharging can occur rapidly, such as in less than 60 minutes. In some embodiments, the power storage devices 136 are recharge in a range from about 5 minutes to about 60 minutes. In other embodiments, recharging occurs in less than 45 minutes, 30 minutes, or 15 minutes. A partial recharge can occur even more rapidly. As a result, a brief recharge of 1 to 5 minutes may be suitable to power the electronic device 102 for an hour or more.

An elongate support structure 137 is provided in some embodiments to support the power storage devices 136. For example, the power storage devices 136 are coupled to the elongate support structure by fasteners, such as adhesive, clips, straps, bands, or other fastening devices. The elongate support structure 137 also aids in the insertion and removal of the power storage devices 136 into and from the support structure 112. One or more electrical conductors are used in some embodiments to electrically connect the power storage devices 136 together and to the power supply electronics 138. In some embodiments, the electrical conductors are connected to the elongate support structure 137.

In addition to the power storage devices 136, some embodiments of the power supply 120 also include power supply electronics 138. In this example, the power supply electronics 138 are arranged within the interior space 134 of the storage region 114, although the power supply electronics can be arranged in other locations of the mobile cart 104 in other embodiments. A more detailed example of the power supply electronics 138 is illustrated and described herein with reference to FIG. 4.

Figure 4:
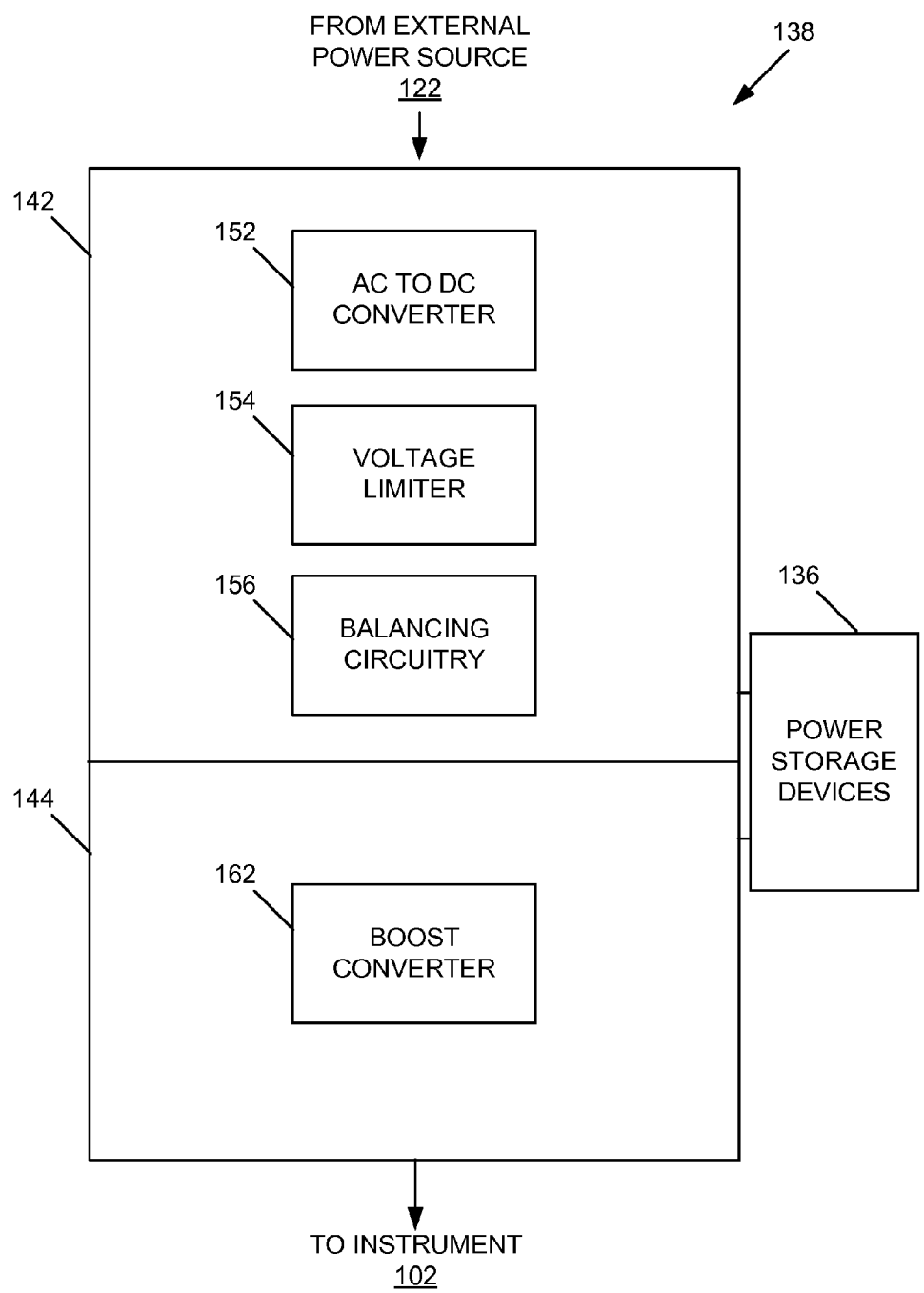
FIG. 4 is a schematic block diagram illustrating an example of the power supply electronics and an example of the power storage devices of the mobile system shown in FIG. 1.

FIG. 4 is a schematic block diagram illustrating an example of the power supply electronics 138 and also illustrating the power storage devices 136. In this example, the power supply electronics 138 include input circuitry 142 and output circuitry 144.

The input circuitry 142 is configured to receive electrical energy from the external power source 122 and supply the electrical energy in an appropriate form to the power storage devices 136.

In some embodiments, the input circuitry 142 includes an AC to DC converter 152, a voltage limiter 154, and balancing circuitry 156.

The AC to DC converter 152 converts the energy from an alternating current form into a direct current form. For example, when the external power source 122 is mains power, the alternating current may have a frequency of 60 Hertz and a voltage of 120V or 220V. The AC to DC converter rectifies the electrical energy into a direct current form, such as having a voltage in a range from about 3V to about 12V.

In some embodiments, the input circuitry 142 includes a voltage limiter 154. The voltage limiter 154 operates to limit the maximum voltage that can be applied by the input circuitry 142 to the power storage devices 136. Capacitors can be damaged if the voltage applied to them exceeds a certain voltage. The voltage limiter 154 is configured to ensure that the maximum voltage provided by the input circuitry 142 does not exceed the maximum voltage ratings of the capacitors.

In some embodiments, capacitors of the power storage devices 136 are arranged in series. In such cases, the maximum voltage applied across a set of series-connected capacitors is the sum of the maximum voltages of each of the capacitors. In this example, the voltage limiter 154 is configured to limit the maximum voltage applied to the set of capacitors to less than or equal to the sum of the maximum voltage ratings of the capacitors.

In some embodiments, the input circuitry 142 includes balancing circuitry 156. The balancing circuitry 156 operates to ensure that the maximum voltage applied to an individual capacitor does not exceed that capacitor's maximum voltage rating. For example, when several capacitors are arranged in series, the total voltage applied across the set of series-connected capacitors may exceed the maximum voltage of an individual capacitor. The balancing circuitry 156 operates to protect the individual capacitors to ensure that the voltage applied to the respective capacitor does not exceed that capacitors maximum voltage rating.

The output of the input circuitry 142 is supplied to the power storage device 136 to recharge the power storage devices.

The output circuitry operates to deliver the electrical energy stored in the power storage devices 136 to the electronic device 102. In this example, the output circuitry 144 includes a boost converter 162.

The boost converter 162 operates to convert the electrical energy from the power storage devices 136 into a form suitable for use by the electronic device 102. For example, the voltage output from capacitors decays rapidly over time. Many electronic device 102, however, are designed to operate with a more constant voltage. Therefore, the boost converter 162 operates to convert the output from the power storage device 136 into a substantially constant voltage output, which can be supplied to the electronic device 102.

In another possible embodiment, the output circuitry 144 includes a mimic circuit. The mimic circuit operates to supply an output voltage that mimics the output voltage of one or more batteries. The mimic circuit is useful when the output circuitry 144 is being used to power an electronic device 102 that is designed to detect and alert a user to when the energy remaining in a battery powering the electronic device 102 is running low. The mimic circuit operates to detect the voltage output from the power storage devices 136 and to generate an output voltage curve that mimics output that would be provided by a battery having a similar energy level. An example of a mimic circuit is described in more detail in U.S. patent application Ser. No. 13/650,488, filed on Oct. 12, 2012, and titled MOTION SENSITIVE AND CAPACITOR POWERED HANDHELD DEVICE, the disclosure of which is incorporated by reference herein in its entirety. In summary, in some embodiments the mimic circuitry includes a microprocessor that converts the output voltage from the power storage devices 136 to a different output voltage based on a lookup table.

Figure 5:
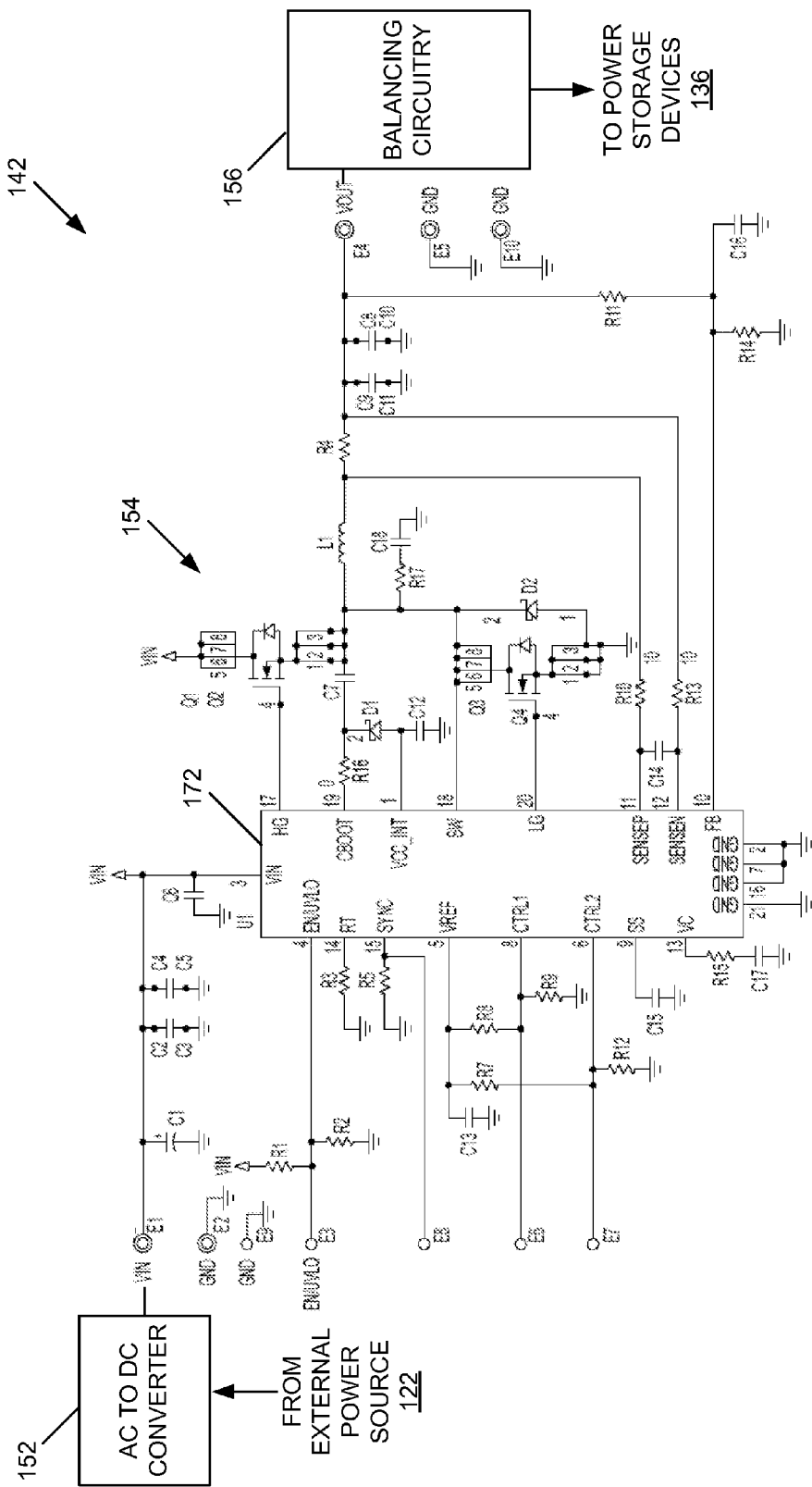
FIG. 5 is a schematic diagram illustrating an example of the input circuitry of the power supply electronics shown in FIG. 4.

FIG. 5 is a schematic diagram illustrating an example of the input circuitry 142. In some embodiments, the input circuitry 142 includes the AC to DC converter 152, voltage limiter 154, and balancing circuitry 156. In this example, the input circuitry 142 includes a step-down controller 172 and other electronic components 174.

The AC to DC converter receives power from the external power source 122 in an AC form and converts that power into a DC form. For example, in some embodiments the power is mains power, such as received through a power cable and plug coupled to a wall receptacle, which receives 120V or 240V AC power, for example.

The voltage limiter 154 then operates to reduce the voltage to a voltage suitable for supply to the power storage devices 136. In this example, the voltage limiter includes a step-down controller 172. One example of a suitable step down controller is the High Power, Constant Current, Constant Voltage, Step-Down Controller, Part No. LT3741EFE, available from Linear Technology, Inc. of Milpitas, Calif. The voltage limit set by the voltage limiter 154 is selected depending on the configuration and type of power storage devices 136 that are used. The voltage limit is selected to ensure that the maximum voltage ratings of the capacitors are not exceeded.

In another possible embodiment, the input circuitry 142 includes a current limiter circuit. The current limiter circuit limits the current supplied by the input circuitry to the power storage devices 136. The current limiter can be included in place of the voltage limiter 154 in one embodiment, or in addition to the voltage limiter 154 in another embodiment.

The output from the voltage limiter 154 is then provided to the balancing circuitry 156 and to the power storage devices 136.

In some embodiments, other electronic components 174 are included and connected as shown in FIG. 5. Other embodiments have other configurations.

Figure 6:
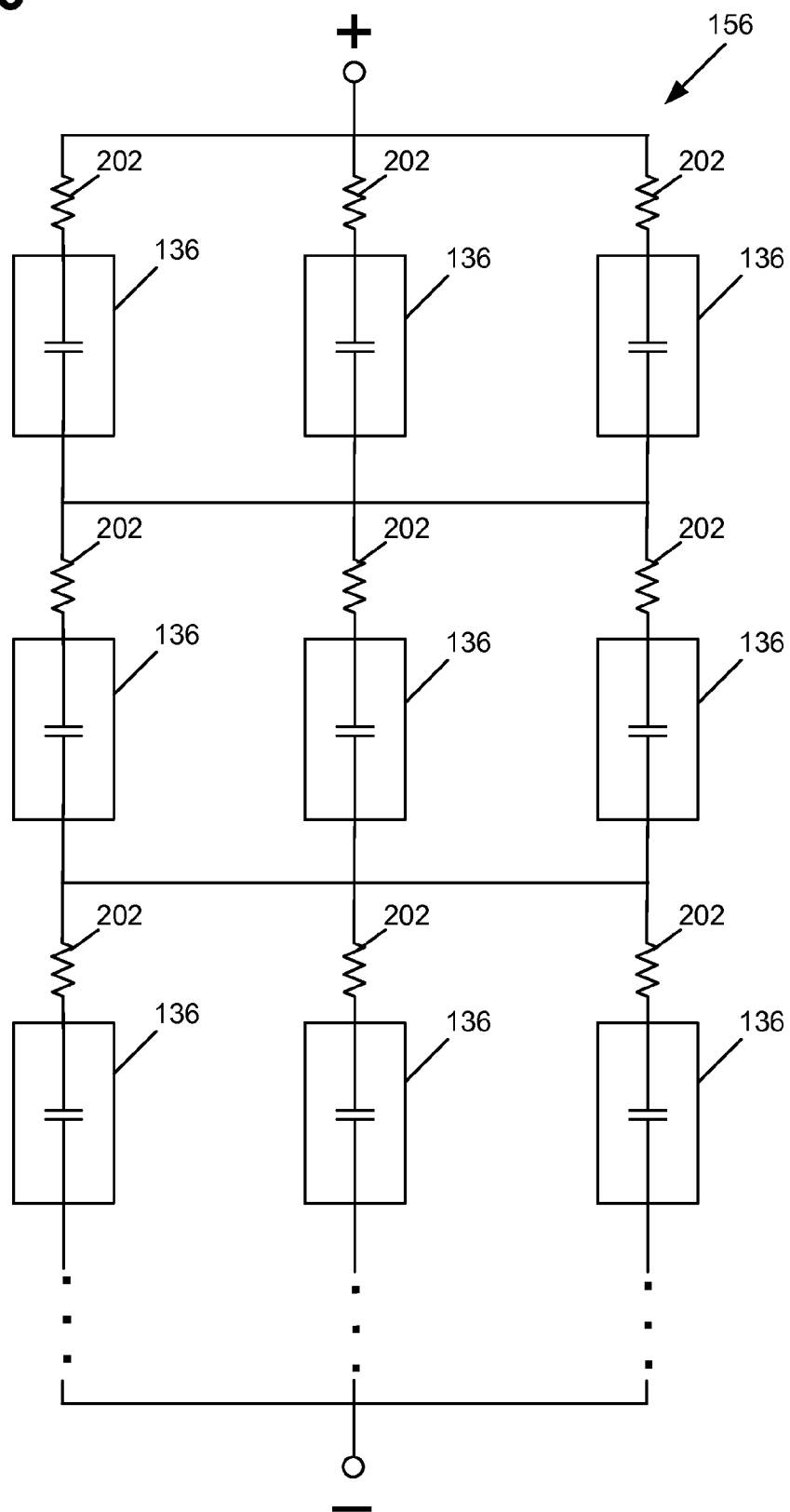
FIG. 6 is a schematic diagram illustrating an example of balancing circuitry of the input circuitry shown in FIG. 5.

FIG. 6 is a schematic diagram illustrating an example of the balancing circuitry 156 of the input circuitry shown in FIG. 5. This example includes power storage devices 136 in the form of capacitors, as well as resistors 202 and electrical conductors. The diagram illustrates only one possible configuration, and various other configurations are possible.

In this example, banks of three capacitors 136 are connected in parallel and then each of the banks of three capacitors 136 are arranged in series with other banks of capacitors 136. Any number of banks of capacitors 136 can be arranged in series, as desired. In addition a resistor 202 is arranged in series with the positive terminal of the capacitor 136. The resistors 202 operate to balance the power supplied to each capacitor 136.

In a basic configuration, the balancing circuitry includes series and parallel resistors 202 that match the impedance between the capacitors 136. Since all capacitors 136 are made at least slightly differently and are sensitive to over voltage, such that when you have a string of them in series the one with the lowest impedance will reach its max rated voltage first and if left unchecked, will over fill the capacitor 136 and ultimately shorten its life. The balancing circuitry 156 operates to match the impedance of the capacitors to prevent this and allow each capacitor 136 to charge in an equal fashion. A more sophisticated version can be made using field-effect transistors that act like resistors and can be controlled by a microprocessor in a smart adaptation where the voltage at each capacitor 136 is read through an A/D converter.

In another possible embodiment, the capacitors 136 are measured prior to the assembly of each system and pre-matched with predetermined fixed resistors 202 and never changed.

Figure 7:
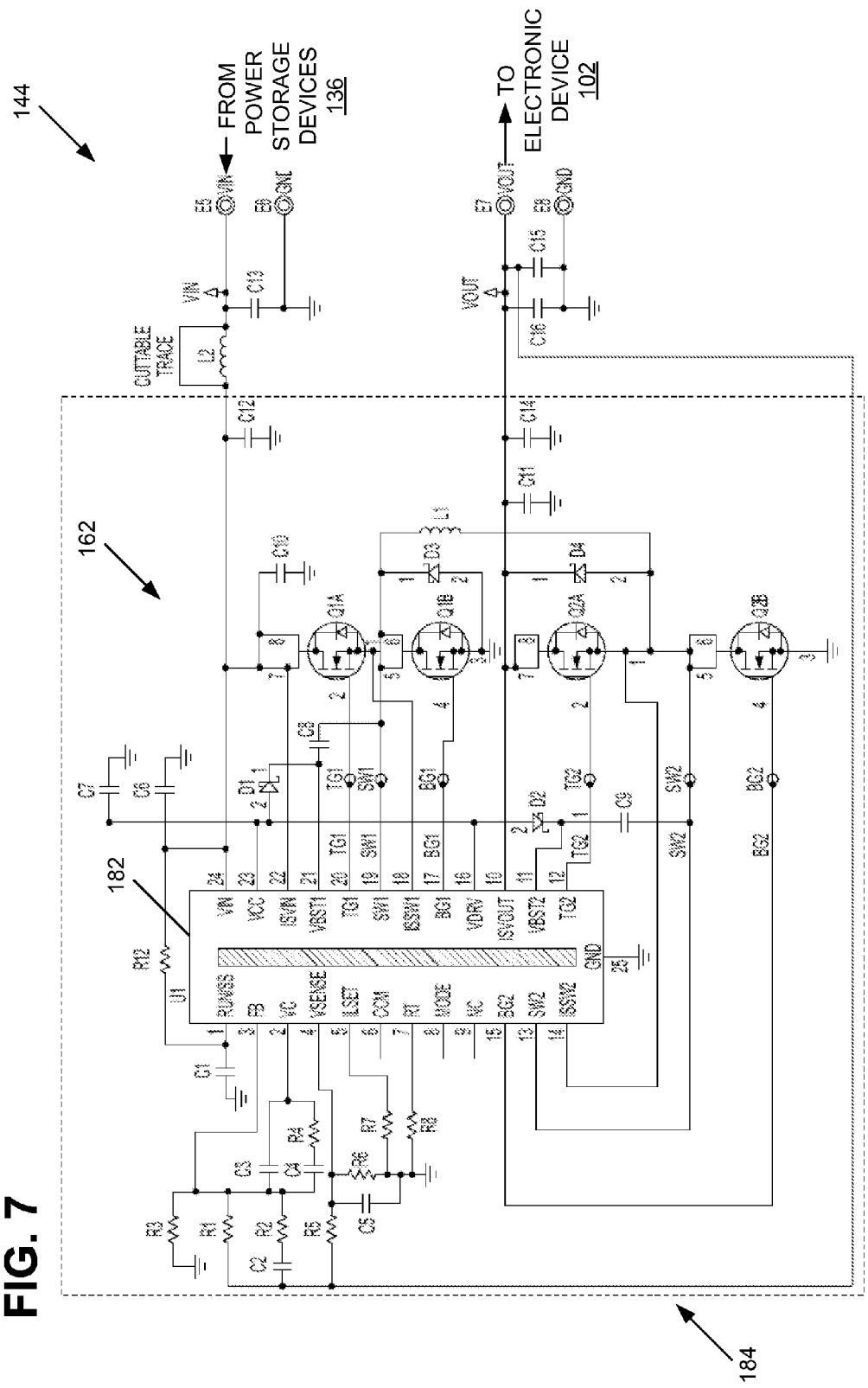
FIG. 7 is a schematic diagram illustrating an example of the output circuitry of the power supply electronics shown in FIG. 4.

FIG. 7 is a schematic diagram illustrating an example of the output circuitry 144. The output circuitry 144 receives energy from the power storage devices 136 and delivers the energy to the electronic device 102 in a suitable form. In this example, the output circuitry 144 includes a boost converter 162 including a buck-boost controller 182 and other electronic circuitry 184.

One example of a suitable buck-boost controller 182 is the High Efficiency, Synchronous, No $R_{SENSE}$, Buck-Boost Controller, Part No. LTC3785, available from Linear Technology, Inc. of Milpitas, Calif.

In some embodiments, other electronic circuitry 184 are included and connected as illustrated in FIG. 7. Other embodiments have other configurations.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A mobile cart for an electronic device, the mobile cart comprising:
   a stand having an outer perimeter;
   a wheeled base section having an outer perimeter;
   a vertical support structure centrally positioned relative to the stand and the wheeled base section and extending vertically intermediate the base and the stand, the vertical support structure having an outer perimeter smaller than the outer perimeter of either the stand or the wheel base section and configured to support a weight of the electronic device, the vertical support structure having an interior space;
   a removably insertable support structure that is removably insertable within the vertical support structure;
   a plurality of capacitor power storage devices coupled to the removably insertable support structure and presented in an arrangement in the interior space of the vertical support structure when the removably insertable support structure is inserted in the vertical support structure; and
   power supply electronics including:
      input circuitry configured to receive electrical energy from an external power source and to recharge the capacitor power storage devices; and
      output circuitry configured to supply electrical energy from the capacitor power storage devices to power the electronic device supported by the mobile cart.

2. The mobile cart of claim 1, wherein the capacitor power storage devices are super capacitors or ultra capacitors.

3. The mobile cart of claim 1, wherein the capacitor power storage devices have capacities of greater than 100 Farads.

4. The mobile cart of claim 1, wherein the input circuitry further comprises an AC to DC converter.

5. The mobile cart of claim 4, wherein the input circuitry further comprises a voltage limiter configured to limit a maximum voltage supplied to the capacitor power storage devices.

6. The mobile cart of claim 4, wherein the input circuitry further comprises a current limiter configured to limit a maximum current supplied to the capacitor power storage devices.

7. The mobile cart of claim 1, wherein the input circuitry further comprises balancing circuitry configured to limit a maximum voltage applied to each of the capacitor power storage devices.

8. The mobile cart of claim 7, wherein the capacitor power storage devices are configured in banks of capacitors connected in parallel, wherein the banks of capacitors are connected in series with the other banks of capacitors, and further comprising series resistors connected to the positive terminal of each of the capacitors.

9. The mobile cart of claim 1, further comprising a storage region connected to the vertical support structure and including a second interior space, wherein the power supply electronics are at least partially contained within the second interior space of the storage region.

10. The mobile cart of claim 1, wherein the vertical support structure is a hollow cylindrical tube.

11. The mobile cart of claim 1, wherein the capacitor power storage devices collectively have a capacity in a range from 1,000 Farads to 50,000 Farads.

12. The mobile cart of claim 1, wherein the input circuitry further comprises a step-down controller.

13. The mobile cart of claim 1, wherein the output circuitry further comprises a boost converter.

14. The mobile cart of claim 13, wherein the boost converter comprises a buck-boost converter.

15. The mobile cart of claim 1, wherein the removably insertable support structure is removably insertable within the vertical support structure through an opening in the wheel base section.

16. A mobile system comprising:
    a medical instrument; and
    a mobile cart supporting the medical instrument, the mobile cart comprising:
        a stand having an outer perimeter;
        a wheeled base section having an outer perimeter;
        a vertical support structure centrally positioned relative to the stand and the wheel base section and extending vertically intermediate the base and the stand, the vertical support structure having an outer perimeter smaller than the outer perimeter of either the stand or the wheel base section and configured to support the medical instrument in a spaced relationship to the base, the vertical support structure having an interior space;
        a removably insertable support structure that is removably insertable within the vertical support structure;
        a plurality of capacitor power storage devices coupled to the removably insertable support structure and presented in an arrangement in the interior space of the vertical support structure when the removably insertable support structure is inserted in the vertical support structure; and
    power supply electronics including:
        input circuitry configured to receive electrical energy from an external power source and to recharge the capacitor power storage devices; and
        output circuitry electrically coupled to the medical instrument to supply electrical energy from the capacitor power storage devices to the medical instrument.

17. The mobile system of claim 16, wherein the medical instrument is a patient monitor.

18. The mobile system of claim 17, wherein the patient monitor is a vital signs monitor.

19. A method of powering an electronic device with a mobile cart, the method comprising:
    receiving energy at the mobile cart from an external source;
    storing the energy in capacitors, the capacitors being coupled to a removably insertable support structure that is inserted into a vertical support structure of the mobile carte, the removably insertable support structure operating to position the capacitors along an elongate vertical length of an interior space of the vertical support structure of the mobile cart, the vertical support structure configured to support a weight of the electronic device via central positioning of the vertical support structure relative to a stand and the wheel base section of the mobile cart, the stand configured to be placed beneath the electronic device;
    converting the energy from the capacitors into a form suitable for delivery to the electronic device; and
    supplying the energy to the electronic device from the mobile cart.

20. The method of claim 19, wherein receiving energy at the mobile cart occurs for a period of less than 15 minutes to recharge the capacitors from a substantially depleted state to a substantially fully charged state.

* * * * *